(12) United States Patent
Aoki et al.

(10) Patent No.: US 6,872,397 B2
(45) Date of Patent: Mar. 29, 2005

(54) METHOD FOR TREATING NEUROMUSCULAR DISORDERS AND CONDITIONS WITH BOTULINUM TOXIN TYPES A AND B

(75) Inventors: K. Roger Aoki, Laguna Hills, CA (US); Michael W. Grayston, Irvine, CA (US); Steven R. Carlson, Laguna Nigel, CA (US); Judith M. Leon, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 09/812,113

(22) Filed: Mar. 15, 2001

(65) Prior Publication Data

US 2001/0012833 A1 Aug. 9, 2001

Related U.S. Application Data

(63) Continuation of application No. 08/075,048, filed on Jun. 10, 1993.

(51) Int. Cl.$^7$ ......................... A61K 39/08; A61K 39/02; A01N 37/18
(52) U.S. Cl. ............................... 424/239.1; 424/234.1; 424/236.1; 424/247.1; 424/190.1; 514/2
(58) Field of Search .......................... 424/190.1, 234.1, 424/236.1, 239.1, 247.1; 514/2

(56) References Cited

U.S. PATENT DOCUMENTS

| | | |
|---|---|---|
| 5,183,462 A | 2/1993 | Borodic |
| 5,298,019 A | 3/1994 | Borodic |
| 5,401,243 A | 3/1995 | Borodic |
| 5,696,077 A | 12/1997 | Johnson et al. |

FOREIGN PATENT DOCUMENTS

| | | |
|---|---|---|
| WO | WO 94/0081 A | 1/1994 |
| WO | WO 94/00481 | 1/1994 |
| WO | WO 94/28922 | 12/1994 |
| WO | WO 95/17904 | 7/1995 |

OTHER PUBLICATIONS

Jankovic et al., 1991, New England J. of medicine, vol. 324, No. 17, pp. 1186–1194.*
Ludlow et al., 1992, New England J. of medicine, vol. 326, No. 5, pp. 349–350.*
Simpson, L., 1981., Pharmacol. Reviews, vol. 33, No. 3, pp. 155–188.*
The Merck Manual of diagnosis and therapy, 1987. Merck Sharp and Dohme Researck Laboratories, NJ. pp. 1449–1551, 1420–1421.*
Athena files US and Canadian Investigational New Drugs (INDs); Scrip Jun. 5, 1992; No. 1724, p29.
Athena Makers a Wise Move; Medical Advertising News, Nov. 1992, p4.
Athena Outlines Business Strategy; Marketletter; Oct. 5, 1992, p N/A.
Blasl, Juan et al.; *Botulinum Neurotoxin A Selectively Cleaves the Synaptic Protein SNAP—25; Nature;* vol. 365, Sep. 9, 1993, pp160–163.
Brin, Mitchell; *Interventional Neurology; Treatment of Neurological Conditions With Local Infection of Botulinum Toxin; Arch. De Neurobiol.;* 54, Supl. 3, 1991 pp 7–23.
Dasgupta, Bibhuti; *The Structure of Botulinum Neurotoxin; Botulinum Neurotoxin and Tetanus Toxin;* Edited by Simpson, Lance; pp 53–67, 1989.
Gjerstad, Leif et al.; *Treatment of Focal Dystonias With Botulinum Toxin;* Translation Attached; *Tidsskr Nor Laegeforen nr;* 21, 1991; 111; pp2637–2639.
Jankovic, Joseph et al.; *Therapeutic User of Botulinum Toxin; The New England Journal of Medicine;* Apr. 25, 1991, pp 1186–1991.
Moyer, Elizabeth et al.; *Botulinum Toxin Type B: Experimental and Clinical Experience; Therapy With botulinum Toxin;* Edited by Jankovic, Joseph et al.; pp 71–85, 1994.
Moyer, E. D. et al.; *Effects of Intramuscular Injection of Botulinum Toxin Type B in Nonhuman Primates: Botulinum and Tetanus Neurotoxins;* Edited by Dasgupta, B. R., pp665–666, 1992.
National Institutes of Health Consensus Development Conference Statement: *Clinical Use of Botulinum Toxin*: http://text.nlm.nih.gov/nih/cdc/www/83txt.html ; 18 pp. 1–18, 1990.
Poewe, W. et al.: *Experience with Botulinum Toxin in Cervical Dystonia; Therapy with Botulinum Toxin;* Edited by Jankovic, Joseph, pp 267–278, 1994.
Schantz, Edward et al.; *Properties and Use of Botulinum Toxin and Other Microbial Neurotoxins in Medicine; American Society for Microbiology;* vol. 56, 1992, pp 80–95.
Scott, Alan B. et al.: *Systemic Toxicity of Botulinum Toxin by Intramuscular Injection in the Monkey; Movement Disorders;* vol. 3, No. 4, 1988, pp 333–335.
Simpson, Lance L.; *Clinically Relevant Aspects of the Mechanism of Action of Botulinum Neurotoxin; Journal of Voice,* vol. 6, No. 4, 1992, pp 358–364.
Simpson, Lance L.; *The Origin Structure, and Pharmacological Activity of Botulinum Toxin; Pharmacological Reviews,* vol. 33, No. 3, pp155–188, 1981.

(Continued)

*Primary Examiner*—Yvonne Eyler
*Assistant Examiner*—Olga N. Chernyshev
(74) *Attorney, Agent, or Firm*—Stephen Donovan

(57) ABSTRACT

A method of treating a patient suffering from a disease, disorder or condition includes the administration to the patient of a therapeutically effective amount of botulinum toxin of a selected serotype until the patient experiences loss of clinical response to the administered botulinum toxin and thereafter administering to the patient a therapeutically effective amount of another botulinum toxin of a different serotype.

5 Claims, No Drawings

OTHER PUBLICATIONS

Tsui, J.K. et al.: *A Pilot Study on the Use of Botulinum Toxin in Spasmodic Torticollis;* The Canadian Journal of Neurological Sciences, vol. 12, No. 4, Nov. 1985, pp 314–316.

Tsui, J.K. et al.: *Botulinum Toxin Type B in the Treatment of Cervical Dystonia: A Pilot Study;* Neurology, Nov. 1995, 45(11). pp 2109–2110.

Tsui, J.K. et al.: *Local Treatment of Spasmodic Torticollis with Botulinum Toxin:* Le Journal Canadien Des Sciences Neurologiques, vol. 14, No. 3 (Supplement), Aug. 1987. pp 533–535.

U.S. Food and Drug Administration; *List of Orphan Designations and Approvals:* http://www.fda.gov/orphan/designat/list.htm, 1984–1999, 6 pp out of 257.

Borodic, G.E., et al., *Botulinum B Toxin as an alternative to Botulinum A Toxin: A Histologic Study*, Ophthalmic Plastic and Reconstructive Surgery, vol. 9, No. 3, pp 182–190, 1993.

Schantz, E.J., et al., *Properties and use of botulinum toxin and other microbial neurotoxins in medicine*, Microbiological Reviews, Mar. 1992, pp. 80–99, vol. 56, No. 1.

Sellin, L.C., et al., *Different effects of types A and B botulinum toxin on transmitter release at the rat neuromuscular junction*, Acta Physiolo Scand 1983, 119:127–133.

\* cited by examiner

METHOD FOR TREATING NEUROMUSCULAR DISORDERS AND CONDITIONS WITH BOTULINUM TOXIN TYPES A AND B

CROSS REFERENCE

This application is a continuation of Ser. No. 08/075,048, filed Jun. 10, 1993.

FIELD OF THE INVENTION

The present invention provides novel methods for treating diseases of the nervous system, e.g., neuromuscular disorders and conditions, with botulinum toxins. In addition, the present invention provides methods useful in all tissue and organ systems which involve the release of neurotransmitters, especially acetylcholine. These cholinergic transmission systems include neuromuscular junctions (muscles), smooth muscles (gut, sphincters, etc.) and secretions (salivation and mucus).

BACKGROUND OF THE INVENTION

A bacterial toxin, botulinum toxin, in particular botulinum toxin type A, has been used in the treatment of a number of neuromuscular disorders and conditions involving muscular spasm; for example, strabismus, blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in local paralysis and hence relaxation of the muscle afflicted by spasm.

For one example of treating neuromuscular disorders, see U.S. Pat. No. 5,053,005 to Borodic, which suggests treating curvature of the juvenile spine, i.e., scoliosis, with an acetylcholine release inhibitor, preferably botulinum toxin A.

For the treatment of strabismus with botulinum toxin type A, see Elston, J. S., et al., *British Journal of Ophthalmology*, 1985, 69, 718–724 and 891–896. For the treatment of blepharospasm with botulinum toxin type A, see Adenis, J. P., et al., *J. Fr. Ophthalmol.*, 1990, 13 (5) at pages 259–264. For treating squint, see Elston, J. S., *Eye*, 1990, 4(4):VII. For treating spasmodic and oromandibular dystonia torticollis, see Jankovic et al., *Neurology*, 1987, 37, 616–623.

Spasmodic dysphonia has been treated with botulinum toxin type A. See Blitzer et al., *Ann. Otol. Rhino. Laryngol*, 1985, 94, 591–594. Lingual dystonia was treated with botulinum toxin type A according to Brin et al., *Adv. Neurol.* (1987) 50, 599–608. Finally, Cohen et al., *Neurology* (1987) 37 (Suppl. 1), 123–4, discloses the treatment of writer's cramp with botulinum toxin type A.

The term botulinum toxin is a generic term embracing the family of toxins produced by the anaerobic bacterium *Clostridium botulinum* and, to date, seven immunologically distinct neurotoxins serotype have been identified. These have been given the designations A, B, C, D, E, F and G. For further information concerning the properties of the various botulinum toxins, reference is made to the article by Jankovic and Brin, *The New England Journal of Medicine*, No. 17, 1990, pp. 1186–1194, and to the review by Charles L. Hatheway in Chapter 1 of the book entitled *Botulinum Neurotoxin and Tetanus Toxin*, L. L. Simpson, Ed., published by Academic Press Inc. of San Diego, Calif., 1989, the disclosures in which are incorporated herein by reference.

The neurotoxic component of botulinum toxin has a molecular weight of about 150 kilodaltons and is thought to comprise a short polypeptide chain of about 50 kD which is considered to be responsible for the toxic properties of the toxin, i.e., by interfering with the exocytosis of acetylcholine, by decreasing the frequency of acetylcholine release, and a larger polypeptide chain of about 100 kD which is believed to be necessary to enable the toxin to bind to the pre-synaptic membrane. The "short" and "long" chains are linked together by means of a simple disulfid bridge. (It is noted that certain serotype of botulinum toxin, e.g., type E, may exist in the form of a single chain un-nicked protein, as opposed to a dichain. The single chain form is less active but may be converted to the corresponding dichain by nicking with a protease, e.g., trypsin. Both the single and the dichain are useful in the method of the present invention.)

Immunotoxin conjugates of ricin and antibodies, which are characterized as having enhanced cytotoxicity through improving cell surface affinity, are disclosed in European Patent Specification 0 129 434. The inventors note that botulinum may be utilized in place of ricin.

Botulinum toxin is obtained commercially by establishing and crowing cultures of *C. botulinum* in a fermenter and then harvesting and purifying the fermented mixture in accordance with known techniques.

Botulinum toxin type A, the toxin type generally utilized in treating neuromuscular conditions, is currently available commercially from several sources; for example, from Port Products Ltd. UK, under the trade name "DYSPORT," and from Allergan, Inc., Irvine, Calif., under the trade name BOTOX®.

It has been found, however, that some patients experience a loss of clinical responsiveness to botulinum toxin injections. One explanation for this action is that the patient has developed neutralizing antibodies or an immune response to, for example, botulinum toxin type A. Alternatively, the type of immune response may be different from just neutralizing antibodies. These include: (1) Allergic reaction where there is immediate local swelling, redness and itching. This may also be associated with general flu-like symptoms. (2) A delayed-type hypersensitivity manifested as swelling and redness at the injection site 48 to 72 hours after injection. (3) Or, a serum sickness-like response where the patient experiences flu-like symptoms. All of these immune-based reactions to type A dictate alternate serotype therapy to maintain clinical benefits.

A further hypothesis may explain loss of clinical responsiveness to botulinum toxin injections. This does not include interaction of other medications which may interfere with the action of botulinum toxin (i.e., angiotensin converting enzyme inhibitor class of antihypertensives and other endopeptidase inhibitors, aminopyridines, acetylcholine esterase inhibitors, etc.). One possible explanation for the loss of responsiveness is an alteration in the neuronal binding of toxin to the presynaptic cholinergic nerve terminal. An alternation of gangliocides could reduce the binding efficacy of the toxin and thus reduce the amount of toxin internalized. Alternatively, an induction of proteases may cause an enhanced breakdown of the toxin either in the extracellular milieu or within the neuron. Finally, the neuron may change the amino acid composition of the target protein for the light chain of the toxin to reduce or eliminate its effect on the exocytotic mechanism.

It is one object of the invention to provide novel treatments of neuromuscular disorders and conditions with botulinum toxin type A followed with treatments of botulinum toxin types B, C, D, E, F and G.

SUMMARY OF THE INVENTION

The present invention provides a method of treating a neuromuscular disorder or condition such as strabismus and other disorders of ocular motility, e.g., comitant and vertical strabismus, lateral rectus palsy, nystagmus, dysthyroid myopathy, etc.; dystonia, e.g., focal dystonias such as spasmodic torticollis, writer's cramp, blepharospasm, oromandibular dystonia and the symptoms thereof, e.g., bruxism, Wilson's disease, tardive dystonia, laryngeal dystonia etc.; other dystonias, e.g., tremor, tics, segmental myoclonus; spasms, such as spasticity due to chronic multiple sclerosis, spasticity resulting in abnormal bladder control, e.g., in patients with spinal cord injury, animus, back spasm, charley horse etc.; tension headaches; levator pelvic syndrome; spina bifida, tardive dyskinesia; Parkinson's and limb (focal) dystonia and stuttering, etc. of a patient, which method comprises administering to the patient suffering from said disorder or condition a therapeutically effective amount of a botulinum A followed with a neurotoxin of a different serotype, i.e., one selected from the group consisting of botulinum toxin types B, C, D, E, F and G.

The clinical features of the above-listed neuromuscular disorders and conditions are described in Jankovic and Brin, cited above, and in Quinn, *Disorders of Movement*, Academic Press, 1989, all of which are incorporated herein by reference.

The present invention further provides compositions of said botulinum toxins in a vehicle suitable for injection of said toxins into the appropriate region of the patient to be treated. Alterations of the vehicle and excipient may include materials designed to retain the injected toxin in the local area.

The present invention further provides a method for treating neuromuscular disorders or conditions in which the patient experiences a loss of clinical response to an initial treatment of botulinum toxin.

More specifically, a method in accordance with the present invention includes administering to the patient a therapeutically effective amount of botulinum toxin of a different serotype until the patient experiences loss of clinical response to the administered botulinum toxin and thereafter administering to the patient another botulinum toxin of the selected serotype, said another botulinum toxin being administered in therapeutically effect amounts.

More particularly, the method in accordance with the present invention includes initial treatment with botulinum toxin type A followed by treatment with another botulinum toxin selected from the group consisting of types B, C, D, E and F.

Alternatively, the initial treatment may be with botulinum toxin type B followed by another botulinum toxin serotype selected from the group consisting of types A, C, D, E and F.

An alternative embodiment of the present invention includes the administration to a patient of a therapeutically effective amount of botulinum toxin of a selected serotype until the patient develops neutralizing antibodies and thereafter administration to the patient of another botulinum toxin of a different serotype, said another botulinum toxin being administered in a therapeutically effective amount.

DETAILED DESCRIPTION

The botulinum toxins used according to the present invention are botulinum toxin serotype A, B, C, D, E, F and G.

Each serotype of botulinum toxin has been identified as immunologically different proteins through the use of specific antibodies. For example, if the antibody (antitoxin) recognizes, that is, neutralizes the biological activity of, for example, type A it will not recognize types B, C, D, E, F or G.

While all of the botulinum toxins appear to be zinc endopeptidases, the mechanism of action of different serotypes, for example, A and E within the neuron appear to be different than that of type B. In addition, the neuronal surface "receptor" for the toxin appears to be different for the serotypes.

The physiologic groups of *Clostridium botulinum* types are listed in Table I.

TABLE I

Physiologic Groups of *Clostridium botulinum*

| Group | Toxin Sero-Type | Biochemistry | Milk Digest | Glucose Fermen-tation | Lipase | Phages & Plasmids | Phenotypically Related Clostridium (nontoxigenic) |
|---|---|---|---|---|---|---|---|
| I | A, B, F | proteolytic saccharolytic | + | + | + | + | *C. sporogenes* |
| II | B, E, F | nonproteolytic saccharolytic psychotrophic | − | + | + | + | |
| III | C, D | nonproteolytic saccharolytic | ± | + | + | + | *C. novyi* |
| IV | G | proteolytic nonsaccharolytic | + | − | − | − | *C. subterminale* |

These toxin types may be produced by selection from the appropriate physiologic group of *Clostridium botulinum* organisms. The organisms designated as Group I are usually referred to as proteolytic and produce botulinum toxins of types A, B and F. The organisms designated as Group II are saccharolytic and produce botulinum toxins of types B, E and F. The organisms designated as Group III produce only botulinum toxin types C and D and are distinguished from organisms of Groups I and II by the production of significant amounts of propionic acid. Group IV organisms only produce neurotoxin of type G.

The production of any and all of the botulinum toxin types A, B, C, D, E, F and G are described in Chapter 1 of *Botulinum Neurotoxin and Tetanus Toxin*, cited above, and/or the references cited therein. Botulinum toxins types B, C, D, E, F and G are also available from various species of clostridia. Currently fourteen species of clostridia are considered pathogenic.

Most of the pathogenic strains produce toxins which are responsible for the various pathological signs and symptoms. Organisms which produce botulinum toxins have been isolated from botulism outbreaks in humans (types A, B, E and F) and animals (types C and D). Their identities were described through the use of specific antitoxins (antibodies) developed against the earlier toxins. Type G toxin was found in soil and has low toxigenicity. However, it has been isolated from autopsy specimens, but thus far there has not been adequate evidence that type G botulism has occurred in humans.

In general, four physiologic groups of *C. botulinum* are recognized (I, II, III, IV). The organisms capable of producing a serologically distinct toxin may come from more than one physiological group. For example, Type B and F toxins can be produced by strains from Group I or II. In addition, other strains of clostridial species (*C. baratii*, type F; *C. butyricum*, type E; *C. novyi*, type $C_1$ or D) have been identified which can produce botulinum neurotoxins.

Preferably, the toxin is administered by means of intramuscular injection directly into a spastic muscle, in the region of the neuromuscular junction, although alternative types of administration (e.g., subcutaneous injection), which can deliver the toxin directly to the affected muscle region, may be employed where appropriate. The toxin can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added. Stabilizers such as human serum albumin may also be included. The formulation may be preserved by means of a suitable pharmaceutically acceptable preservative such as a paraben, although preferably it is unpreserved.

It is preferred that the toxin is formulated in unit dosage form; for example, it can be provided as a sterile solution in a vial or as a vial or sachet containing a lyophilized powder for reconstituting a suitable vehicle such as water for injection.

In one embodiment, the botulinum toxin is formulated in a solution containing saline and pasteurized human serum albumin, which stabilizes the toxin and minimizes loss through non-specific adsorption. The solution is sterile filtered (0.2 micron filter), filled into individual vials and then vacuum-dried to give a sterile lyophilized powder. In use, the powder can be reconstituted by the addition of sterile unpreserved normal saline (sodium chloride 0.9% for injection).

The dose of toxin administered to the patient will depend upon the severity of the condition; e.g., the number of muscle groups requiring treatment, the age and size of the patient and the potency of the toxin. The potency of the toxin is expressed as a multiple of the $LD_{50}$ value for the mouse, one unit (U) of toxin being defined as being the equivalent amount of toxin that kills 50% of a group of 18 to 20 female Swiss-Webster mice, weighing 20 grams each.

The dosages used in human therapeutic applications are roughly proportional to the mass of muscle being injected. Typically, the dose administered to the patient may be up to about 1,000 units; for example, up to about 500 units, and preferably in the range from about 80 to about 460 units per patient per treatment, although smaller of larger doses may be administered in appropriate circumstances.

As the physicians become more familiar with the use of this product, the dose may be changed. In the botulinum toxin type A, available from Porton, DYSPORT, 1 nanogram (ng) contains 40 U. 1 ng of the botulinum toxin type A, available from Allergan, Inc., i.e., BOTOX®, contains 4 U. The potency of botulinum toxin and its long duration of action mean that doses will tend to be administered on an infrequent basis.

Ultimately, however, both the quantity of toxin administered and the frequency of its administration will be at the discretion of the physician responsible for the treatment and will be commensurate with questions of safety and the effects produced by the toxin.

The invention will now be illustrated by reference to the following nonlimiting examples.

In each of the examples, the appropriate muscles of each patient are injected with sterile solutions containing the botulinum toxins. Total patient doses range from 80 U to 460 U. Before injecting any muscle group, careful consideration is given to the anatomy of the muscle group, the aim being to inject the area with the highest concentration of neuromuscular junctions, if known. Before injecting the muscle, the position of the needle in the muscle is confirmed by putting the muscle through its range of motion and observing the resultant motion of the needle end. General anaesthesia, local anaesthesia and sedation are used according to the age of the patient, the number of sites to be injected, and the particular needs of the patient. In accordance with the present invention, multiple injections are necessary to achieve the desired result, due to the patient's experiencing loss of clinical response to an initial treatment. Also, some injections, depending on the muscle to be injected, may require the use of fine, hollow, teflon-coated needles, guided by electromyography.

Following injection, it is noted that there are no systemic or local side effects and none of the patients are found to develop extensive local hypotonicity. The majority of patients show an improvement in function both subjectively and when measured objectively.

EXAMPLE 1

The Use of Botulinum Toxin Serotype A, B and F in the Treatment of Tardive Dyskinesia A patient, suffering from tardive dyskinesia resulting from the treatment with an antipsychotic drug, such as haloperidol, is treated with an effective amount of botulinum toxin type A by direct injection of such toxin into the muscles identified by the physician. After two to four days, the symptoms of tardive dyskinesia, i.e., orofacial dyskinesia, athetosis, dystonia, chorea, tics and facial grimacing, etc., are markedly reduced. Upon continued administration of the botulinum toxin type A, a loss of clinical response is noted. Thereafter, an effective amount of botulinum toxin type B is injected and the symptoms of tardive dyskinesia continue to be markedly reduced.

EXAMPLE 1(a)

The method of Example 1 is repeated, except that a patient suffering from tardive dyskinesia is injected with an effective amount of botulinum toxin type A, followed by injection of an effective amount of botulinum toxin type C. Similar results are obtained.

EXAMPLE 1(b)

The method of Example 1 is repeated, except that a patient suffering from tardive dyskinesia is injected with an effective amount of botulinum toxin type A, followed by injection of an effective amount of botulinum toxin type D. Similar results are obtained.

EXAMPLE 1(c)

The method of Example 1 is repeated, except that a patient suffering from tardive dyskinesia is injected with an effective amount of botulinum toxin type A, followed by injection of an effective amount of botulinum toxin type E. Similar results are obtained.

EXAMPLE 1(d)

The method of Example 1 is repeated, except that a patient suffering from tardive dyskinesia is injected with an effective amount of botulinum toxin type A, followed by injection of an effective amount of botulinum toxin type F. Similar results are obtained.

EXAMPLE 2

Use of Botulinum Toxin in the Treatment of Spasmodic Torticollis

A male, suffering from spasmodic torticollis, as manifested by spasmodic or tonic contractions of the neck musculature, producing stereotyped abnormal deviations of the head, the chin being rotated to one side, and the shoulder being elevated toward the side at which the head is rotated, is treated by injection with up to about 300 units, or more, of botulinum toxin type E, (having an activity of one to four days) in the dystonic neck muscles. After the symptoms are substantially alleviated and the patient is able to hold his head and shoulder in a normal position, the patient develops antibodies. Thereafter the patient is injected with botulinum toxin type B and the symptoms continue to be substantially alleviated.

Although there has been hereinabove described a use of botulinum toxin serotype for treating neuromuscular disorders and conditions in accordance with the present invention, for the purpose of illustrating the manner in which the invention may be used to advantage, it should be appreciated that the invention is not limited thereto since many obvious modifications can be made, and it is intended to include within this invention any such modifications as will fall within the scope of the appended claims. Accordingly, any and all modifications, variations, or equivalent arrangements which may occur to those skilled in the art, should be considered to be within the scope of the present invention as defined in the appended claims.

What is claimed is:

1. A method of treating a patient suffering from a dystonial the method comprising intramuscular or subcutaneous administration to the patient of up to 1,000 units of a botulinum toxin type A per patient treatment session until the patient experiences loss of clinical response to the administered botulinum toxin type A, as determined by a failure of the administered botulinum toxin type A to achieve a marked reduction of or to substantially alleviate a symptom of the dystonia, and thereafter administering to the patient at least about 80 units of a botulinum toxin type B to thereby again achieve a marked reduction or a substantial alleviation of a symptom of the dystonia.

2. The method of claim 1, wherein the dystonia is cervical dystonia.

3. A method of treating cervical dystonia in a patient, the method comprising intramuscular or subcutaneous administration to a patient with dystonia of up to 1,000 units of a botulinum toxin type A per patient treatment session until th patient experiences loss of clinical response to the administered botulinum toxin type A, as determined by a failure of the administered botulinum toxin type A to achieve a marked reduction of a symptom of the cervical dystonia, and thereafter administering to the patient at least about 80 units of a botulinum toxin type B.

4. The method of claim 3, wherein treating the cervical dystonia reduces the severity of an abnormal head position symptom of the cervical dystonia.

5. The method of claim 3, wherein treating the cervical dystonia reduces a neck pain associated with the cervical dystonia.

* * * * *

UNITED STATES PATENT AND TRADEMARK OFFICE
CERTIFICATE OF CORRECTION

PATENT NO. : 6,872,397 B2
DATED : March 29, 2005
INVENTOR(S) : Aoki et al.

It is certified that error appears in the above-identified patent and that said Letters Patent is hereby corrected as shown below:

Column 8,
Lines 7-8, "dystonial" should read -- dystonia --.

Signed and Sealed this

Tenth Day of January, 2006

JON W. DUDAS
*Director of the United States Patent and Trademark Office*